(12) United States Patent
Pieper et al.

(10) Patent No.: US 7,244,742 B2
(45) Date of Patent: *Jul. 17, 2007

(54) PHARMACEUTICAL COMPOSITIONS FOR INHALATION CONTAINING AN ANTICHOLINERGIC, CORTICOSTEROID AND BETAMIMETIC

(75) Inventors: Michael Paul Pieper, Biberach (DE); Christopher John Montague Meade, Bingen (DE); Michel Pairet, Biberach (DE)

(73) Assignee: Boehringer Ingelheim Pharma GmbH & Co KG, Ingelheim (DE)

( * ) Notice: Subject to any disclaimer, the term of this patent is extended or adjusted under 35 U.S.C. 154(b) by 582 days.

This patent is subject to a terminal disclaimer.

(21) Appl. No.: 10/625,129

(22) Filed: Jul. 23, 2003

(65) Prior Publication Data

US 2004/0228805 A1   Nov. 18, 2004

Related U.S. Application Data

(60) Provisional application No. 60/413,177, filed on Sep. 24, 2002.

(30) Foreign Application Priority Data

Aug. 17, 2002   (DE) ................................ 102 37 739

(51) Int. Cl.
  A61K 9/08 (2006.01)
  A61K 9/10 (2006.01)
  A61K 9/12 (2006.01)
  A61K 9/14 (2006.01)
  A61K 9/48 (2006.01)
  A61K 31/40 (2006.01)
  A61K 31/336 (2006.01)
  A61K 31/438 (2006.01)
  A61K 31/439 (2006.01)
  C07D 451/00 (2006.01)
  C07D 451/02 (2006.01)

(52) U.S. Cl. .................... 514/291; 424/45; 424/46; 424/489; 546/10; 546/80; 546/91

(58) Field of Classification Search ............. 424/45, 424/46, 489; 514/291; 546/10, 80, 91
See application file for complete search history.

(56) References Cited

U.S. PATENT DOCUMENTS

| | | |
|---|---|---|
| 6,706,726 B2 | 3/2004 | Meissner et al. |
| 6,747,154 B2 | 6/2004 | Brandenburg et al. |
| 2002/0115680 A1 | 8/2002 | Meissner et al. |
| 2003/0018019 A1 | 1/2003 | Meade et al. |
| 2003/0152523 A1 | 8/2003 | Martin et al. |
| 2003/0223937 A1 | 12/2003 | Banholzer et al. |
| 2004/0002502 A1 | 1/2004 | Banholzer et al. |
| 2004/0010003 A1 | 1/2004 | Banholzer et al. |
| 2004/0024007 A1 | 2/2004 | Pairet et al. |
| 2004/0044020 A1 | 3/2004 | Meade et al. |
| 2004/0048886 A1 | 3/2004 | Meade et al. |
| 2004/0048887 A1 | 3/2004 | Meade et al. |
| 2004/0058650 A1 | 3/2004 | Meade et al. |
| 2004/0087617 A1 | 5/2004 | Meissner et al. |
| 2004/0166065 A1 | 8/2004 | Schmidt |
| 2005/0004228 A1 | 1/2005 | Konetzki |
| 2005/0008578 A1 | 1/2005 | Schmidt |
| 2005/0025718 A1 | 2/2005 | Meade et al. |
| 2005/0101625 A1 | 5/2005 | Boeck et al. |
| 2005/0154006 A1 | 7/2005 | Meade et al. |

(Continued)

FOREIGN PATENT DOCUMENTS

WO    WO 01/58425 A2    8/2001

(Continued)

OTHER PUBLICATIONS

Dutu, S. et al; Lung Function In COPD Patients Under Long Term Inhaled Therapy With Bronchodilator Agents and Beclometasone, European Respiratory Journal, Supp., Bd. 10, Nr. 25, Supp. 20, 1997; XP001147945.

(Continued)

*Primary Examiner*—Johann P. Richter
*Assistant Examiner*—James H. Alstrum-Acevedo
(74) *Attorney, Agent, or Firm*—Michael P. Morris; Mary-Ellen M. Devlin; Wendy Petka

(57) ABSTRACT

A pharmaceutical composition comprising:
  (a) an anticholinergic of formula 1

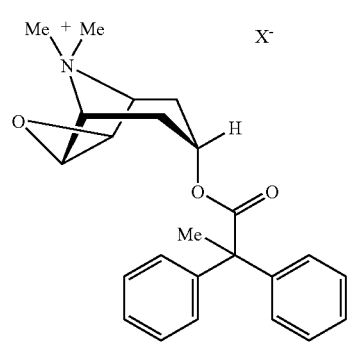

wherein $X^-$ is an anion with a single negative charge;
  (b) a corticosteroid; and
  (c) a betamimetic,
wherein each component (a), (b), and (c) are optionally in the form of the solvates or hydrates thereof, processes for preparing them, and their use in the treatment of respiratory diseases.

21 Claims, 3 Drawing Sheets

U.S. PATENT DOCUMENTS

Figure 1:
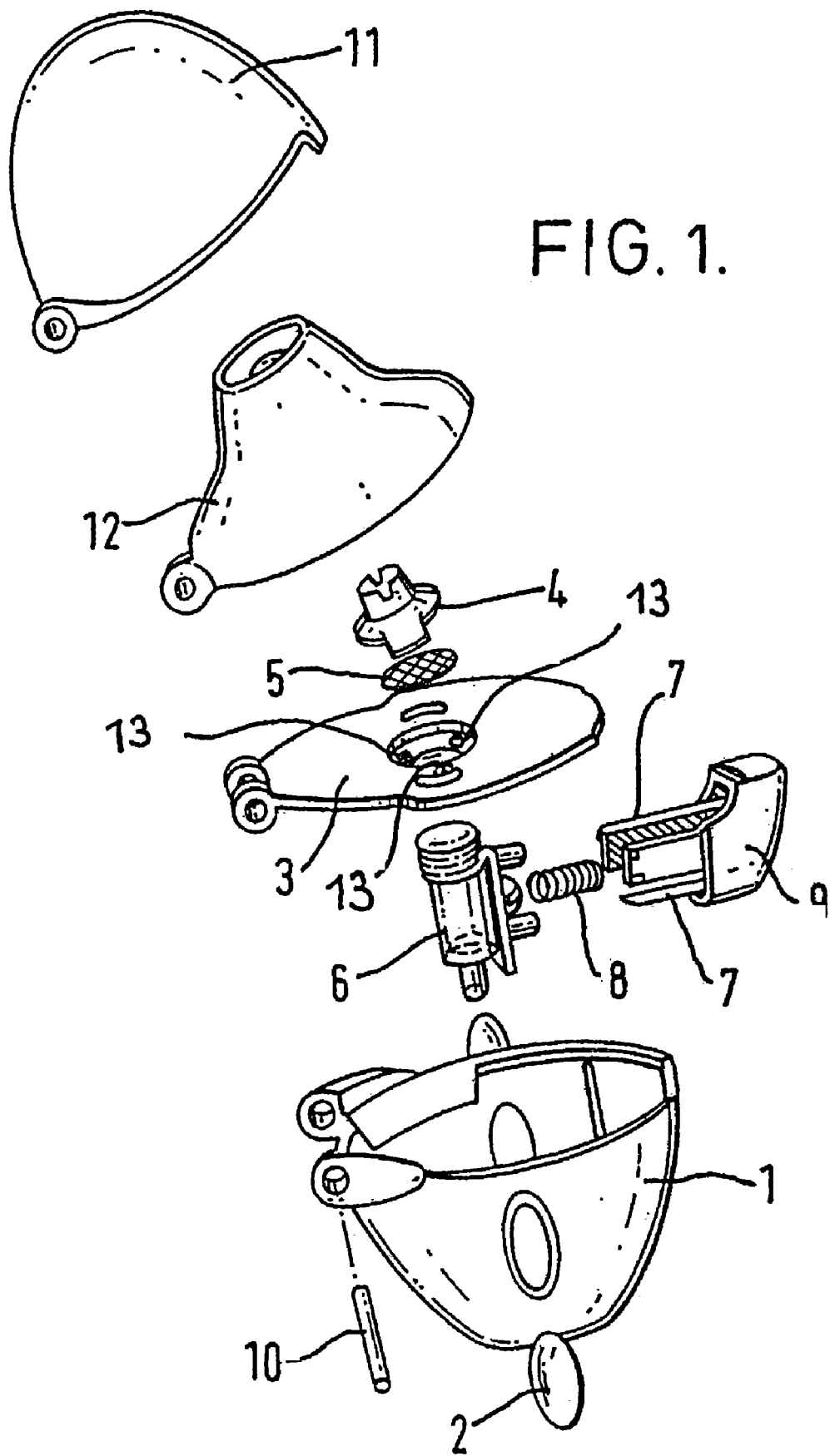

2005/0186175 A1    8/2005   Meade et al.

FOREIGN PATENT DOCUMENTS

| WO | WO 02/32899 A1 | 4/2002 |
| WO | WO 03/000241 A2 | 1/2003 |

OTHER PUBLICATIONS

Balzano, G. et al; "Effectiveness and Acceptability of a Domiciliary Multidrug Inhalation Treatment in Elderly Patients with Chronic Airflow Obstruction: Metered Dose Inhaler Versus Jet Nebulizer"; J. of Aerosol Medicine, vol. 13, No. 1, 2000, pp. 25-33, XP001078735.

PHARMACEUTICAL COMPOSITIONS FOR INHALATION CONTAINING AN ANTICHOLINERGIC, CORTICOSTEROID AND BETAMIMETIC

RELATED APPLICATIONS

This application claims priority to U.S. Ser. No. 60/413,177, filed Sep. 24, 2002, and German Application No. 102 37 739.1, filed Aug. 17, 2002, each of which is hereby incorporated by reference in its entirety.

FIELD OF THE INVENTION

The present invention relates to novel pharmaceutical compositions based on a new anticholinergic, and corticosteroids and betamimetics, processes for preparing them, and their use in the treatment of respiratory diseases.

DESCRIPTION OF THE INVENTION

The present invention relates to novel pharmaceutical compositions for inhalation based on a new anticholinergic, and corticosteroids and betamimetics, processes for preparing them, and their use in the treatment of respiratory diseases.

Surprisingly, an unexpectedly beneficial therapeutic effect, particularly a synergistic effect can be observed in the treatment of inflammatory or obstructive diseases of the respiratory tract if a new anticholinergic is used with one or more corticosteroids and with one or more betamimetics. In view of this synergistic effect, the pharmaceutical combinations according to the invention can be used in smaller doses than would be the case with the individual compounds used in monotherapy in the usual way. This reduces unwanted side effects such as may occur when, for example, corticosteroids and betamimetics are administered.

The effects mentioned above may be observed both when the three active substances are administered simultaneously in a single active substance formulation and when they are administered successively in separate formulations. According to the invention, it is preferable to administer the active substance ingredients simultaneously in a single formulation. The pharmaceutical compositions according to the invention are preferably administered by inhalation according to the invention.

Within the scope of the present invention the anticholinergics used are the salts of formula 1.

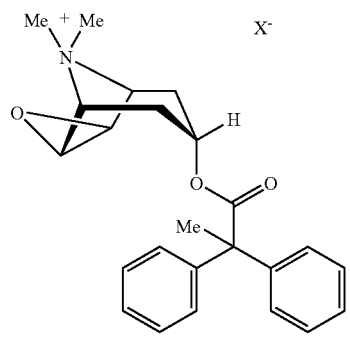

1 wherein:
X⁻ denotes an anion with a single negative charge, preferably an anion selected from the group consisting of chloride, bromide, iodide, sulfate, phosphate, methanesulfonate, nitrate, maleate, acetate, citrate, fumarate, tartrate, oxalate, succinate, benzoate, and p-toluenesulfonate.

Preferably, the salts of formula 1 are used wherein:
X⁻ denotes an anion with a single negative charge selected from the group consisting of chloride, bromide, 4-toluenesulfonate, and methanesulfonate, preferably bromide.

Most preferably, the salts of formula 1 are used wherein:
X⁻ denotes an anion with a single negative charge selected from the group consisting of chloride, bromide, and methanesulfonate, preferably bromide.

Particularly preferred according to the invention is the salt of formula 1 wherein X⁻ denotes bromide.

The salts of formula 1 are known from International Patent Application WO 02/32899. Any reference to the salts of formula 1 includes a reference to any hydrates and solvates thereof which may be obtained.

Within the scope of the present patent application, an explicit reference to the pharmacologically active cation of formula

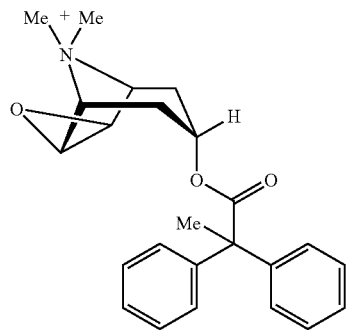

can be recognized by the use of the designation 1'. Any reference to compounds 1 naturally includes a reference to the cation 1'.

Within the scope of the present invention, the word corticosteroids (hereinafter 2) denotes compounds selected from among flunisolide, beclomethasone, triamcinolone, budesonide, fluticasone, mometasone, ciclesonide, rofleponide, GW 215864, KSR 592, ST-126, and dexamethasone. Preferably, compound 2 is selected from among flunisolide, beclomethasone, triamcinolone, budesonide, fluticasone, mometasone, ciclesonide, and dexamethasone. Most preferably, compound 2 is selected from among budesonide, fluticasone, mometasone, and ciclesonide. In some cases, within the scope of the present patent application, the term steroids 2 may also be used on its own instead of the word corticosteroids 2.

Any reference to steroids 2 within the scope of the present invention includes a reference to salts or derivatives 2' which may be formed from the steroids. Examples of possible salts or derivatives 2' include: sodium salts, sulfobenzoates, phosphates, isonicotinates, acetates, propionates, dihydrogen phosphates, palmitates, pivalates, or furoates. In some cases, the compounds of formula 2 may also occur in the form of their hydrates.

Examples of betamimetics 3 which may be used according to the invention include bambuterol, bitolterol, carbuterol, clenbuterol, fenoterol, formoterol, hexoprenaline, ibuterol, pirbuterol, procaterol, reproterol, salmeterol, sulfonterol, terbutaline, tolubuterol, 4-hydroxy-7-[2-{[2-{[3-

(2-phenylethoxy)propyl]sulfonyl}ethyl]amino}ethyl]2 (3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol, or 1-(4-ethoxycarbonylamino-3-cyano-5-fluorophenyl)-2-(tert-butylamino)ethanol.

According to the invention, the following betamimetics 3 are preferably used in the active substance combination: formoterol, salmeterol, 4-hydroxy-7-[2-{[2-{[3-(2-phenylethoxy)propyl]sulfonyl}ethyl]amino }ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, or 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol.

Salmeterol salts or formoterol salts are preferably used as the long-acting betamimetics 3 according to the invention. Any reference to the term betamimetics 3 also includes a reference to the relevant enantiomers or mixtures thereof. For example, any reference to the preferred compounds 3 according to the invention, the salts of salmeterol and formoterol, also includes the relevant enantiomeric salts of R-salmeterol, S-salmeterol, R,R-formoterol, S,S-formoterol, R,S-formoterol, S,R-formoterol, and the mixtures thereof, while the enantiomeric salts of R-salmeterol and R,R-formoterol are of particular importance. The compounds 3 may also be present according to the invention in the form of the hydrates or solvates thereof.

Within the scope of the present invention, any reference to compounds 3 is to be understood as being a reference to physiologically acceptable acid addition salts. By physiologically acceptable acid addition salts of the betamimetics 3 are meant according to the invention pharmaceutically acceptable salts which are selected from the salts of hydrochloric acid, hydrobromic acid, sulfuric acid, phosphoric acid, methanesulfonic acid, acetic acid, fumaric acid, succinic acid, lactic acid, citric acid, tartaric acid, 1-hydroxy-2-naphthalenecarboxylic acid, or maleic acid. If desired, mixtures of the abovementioned acids may be used to prepare the salts 3.

According to the invention, the salts of the betamimetics 3 selected from among the hydrochloride, hydrobromide, sulfate, phosphate, fumarate, methanesulfonate, and xinafoate are preferred. Particularly preferably, in the case of salmeterol, the salts of 3 are selected from those salts which have a solubility in water of 0.1 mg/mL or less, preferably 0.05 mg/mL or less, most preferably 0.04 mg/mL or less. In this context, xinafoate, 4-phenylcinnamate, and diflunisal are mentioned as particularly preferred salts of salmeterol. Particularly preferred salts 3 of salmeterol have a solubility in water of 0.035 mg/mL or less, such as, for example, 4-phenylcinnamate or diflunisal.

Particularly preferably, in the case of formoterol, the salts of 3 are selected from the hydrochloride, sulfate, and fumarate, of which the hydrochloride and fumarate are particularly preferred. Of exceptional importance according to the invention is formoterol fumarate.

If, within the scope of the present invention, there is a reference to betamimetics which are not in the salt form, this can be taken to mean a reference to compounds 3'. For example, the preferred betamimetics 3' according to the invention which are not in salt form are the free base of formoterol or salmeterol, whereas the particularly preferred compounds 3 according to the invention are, for example, salmeterol xinafoate, salmeterol 4-phenylcinnamate, or formoterol fumarate.

Within the scope of the present invention, the betamimetics 3 are optionally also referred to as sympathomimetics or $\beta_2$-receptor agonists ($\beta_2$-agonists). All these names can be regarded as equivalent within the scope of the present invention.

The pharmaceutical combinations of 1, 2, and 3 according to the invention are preferably administered by inhalation. Suitable inhalable powders packed into suitable capsules (inhalettes) may be administered using suitable powder inhalers.

Accordingly, in one aspect, the present invention relates to a pharmaceutical composition which contains a combination of 1, 2, and 3.

In another aspect, the present invention relates to a pharmaceutical composition which contains one or more salts 1, one or more compounds 2 and one or more compounds 3, optionally in the form of their solvates or hydrates. The active substances may be combined in a single preparation or contained in two or three separate formulations. Pharmaceutical compositions which contain the active substances 1, 2, and 3 in a single preparation are preferred according to the invention.

In another aspect, the present invention relates to a pharmaceutical composition which contains, in addition to therapeutically effective quantities of 1, 2, and 3, a pharmaceutically acceptable excipient. In another aspect, the present invention relates to a pharmaceutical composition which does not contain any pharmaceutically acceptable excipient in addition to therapeutically effective quantities of 1, 2, and 3.

The present invention also relates to the use of 1, 2, and 3 for preparing a pharmaceutical composition containing therapeutically effective quantities of 1 2, and 3 for treating inflammatory and/or obstructive diseases of the respiratory tract, particularly asthma and/or chronic obstructive pulmonary disease (COPD), by simultaneous or successive administration. In addition, the pharmaceutical combinations according to the invention may be used to prepare a drug for treating cystic fibrosis or allergic alveolitis (farmer's lung), for example, by simultaneous or successive administration. The combinations of active substances according to the invention will not be used only if treatment with one of the pharmaceutically active ingredients is contraindicated.

The present invention also relates to the simultaneous or successive use of therapeutically effective doses of the combination of the above pharmaceutical compositions 1, 2, and 3 for treating inflammatory or obstructive diseases of the respiratory tract, particularly asthma and/or chronic obstructive pulmonary disease (COPD), provided that treatment with steroids or betamimetics is not contraindicated from a therapeutic point of view, by simultaneous or successive administration. The invention further relates to the simultaneous or successive use of therapeutically effective doses of the combination of the above pharmaceutical compositions 1, 2, and 3 for treating cystic fibrosis or allergic alveolitis (farmer's lung).

In the active substance combinations of 1, 2, and 3 according to the invention, ingredients 1, 2, and 3 may be present in the form of their enantiomers, mixtures of enantiomers or in the form of racemates. For example, the pharmaceutical compositions according to the invention contain the active substances 1, 2, and 3 according to the invention in amounts such that a single administration corresponds to a dosage of the combination of active substances 1, 2, and 3 of 1 µg to 10000 µg, preferably from 10 µg to 2000 µg.

The proportions in which the active substances 1, 2, and 3 may be used in the active substance combinations according to the invention are variable. Active substances 1, 2, and 3 may possibly be present in the form of their solvates or hydrates. Depending on the choice of the compounds 1, 2, and 3, the weight ratios which may be used within the scope of the present invention vary on the basis of the different molecular weights of the various compounds and their different potencies. As a rule, the pharmaceutical combinations according to the invention may contain compounds 1' and 2 in ratios by weight ranging from 1:250 to 250:1, and preferably from 1:150 to 150:1. In the particularly preferred pharmaceutical combinations which contain in addition to 1' a compound selected from among budesonide, fluticasone, mometasone, and ciclesonide as steroid 2, the weight ratios of 1' to 2 are most preferably in a range from about 1:40 to 40:1, and more preferably in the range from 1:30 to 30:1.

For example, without restricting the scope of the invention thereto, preferred combinations of 1 and 2 according to the invention may contain the cation 1' and one of the abovementioned preferred steroids 2 in the following proportions by weight: 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; or 20:1.

The pharmaceutical compositions according to the invention containing the combinations of 1 and 2 are normally administered so that 1' and 2 are present together in doses of 5 µg to 5000 µg, preferably from 10 µg to 2000 µg, more preferably from 15 to 1000 µg, even more preferably from 20 µg to 800 µg, preferably according to the invention from 30 µg to 700 µg, preferably from 40 µg to 600 µg, preferably from 50 µg to 500 µg, preferably from 40 µg to 500 µg, more preferably from 50 µg to 400 µg per single dose. For example, combinations of 1 and 2 according to the invention contain a quantity of 1' and steroid 2 such that the total dosage per single dose is about 35 µg, 45 µg, 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, 260 µg, 265 µg, 270 µg, 275 µg, 280 µg, 285 µg, 290 µg, 295 µg, 300 µg, 305 µg, 310 µg, 315 µg, 320 µg, 325 µg, 330 µg, 335 µg, 340 µg, 345 µg, 350 µg, 355 µg, 360 µg, 365 µg, 370 µg, 375 µg, 380 µg, 385 µg, 390 µg, 395 µg, 400 µg, 405 µg, 410 µg, 415 µg, 420 µg, 425 µg, 430 µg, 435 µg, 440 µg, 445 µg, 450 µg, 455 µg, 460 µg, 465 µg, 470 µg, 475 µg, 480 µg, 485 µg, 490 µg, 495 µg, 500 µg, 505 µg, 510 µg, 515 µg, 520 µg, 525 µg, 530 µg, 535 µg, 540 µg, 545 µg, 550 µg, 555 µg, 560 µg, 565 µg, 570 µg, 575 µg, 580 µg, 585 µg, 590 µg, 595 µg, 600 µg, 605 µg, 610 µg, or the like. It is clear to the skilled man that these proposed dosages per single dose are not to be regarded as being restricted to the numerical values explicitly mentioned. Fluctuations of around ±2.5 µg, particularly fluctuations in the decimal range, are also covered as will be apparent to anyone skilled in the art. In these dosage ranges the active substances 1' and 2 may be present in the weight ratios described above.

For example, and without restricting the scope of the invention thereto, the combinations of 1 and 2 according to the invention may contain an amount of cation 1' and steroid 2 such that each single dose contains 16.5 µg of 1' and 25 µg of 2, 16.5 µg of 1' and 25 µg of 2, 16.5 µg of 1' and 50 µg of 2, 16.5 µg of 1' and 100 µg of 2, 16.5 µg of 1' and 150 µg of 2, 16.5 µg of 1' and 200 µg of 2, 16.5 µg of 1' and 250 µg of 2, 33.0 µg of 1' and 25 µg of 2, 33.0 µg of 1' and 50 µg of 2, 33.0 µg of 1' and 100 µg of 2, 33.0 µg of 1' and 150 µg of 2, 33.0 µg of 1' and 200 µg of 2, 33.0 µg of 1' and 250 µg of 2, 49.5 µg of 1' and 25 µg of 2, 49.5 µg of 1' and 50 µg of 2, 49.5 µg of 1' and 100 µg of 2, 49.5 µg of 1' and 150 µg of 2, 49.5 µg of 1' and 200 µg of 2, 49.5 µg of 1' and 250 µg of 2, 82.6 µg of 1' and 25 µg of 2, 82.6 µg of 1' and 50 µg of 2, 82.6 µg of 1' and 100 µg of 2, 82.6 µg of 1' and 150 µg of 2, 82.6 µg of 1'and 200 µg of 2, 82.6 µg of 1' and 250 µg of 2, 165.1 µg of 1' and 25 µg of 2, 165.1 µg of 1' and 50 µg of 2, 165.1 µg of 1' and 50 µg of 2, 165.1 µg of 1' and 100 µg of 2, 165.1 µg of 1' and 150 µg of 2, 165.1 µg of 1' and 200 µg of 2, 165.1 µg of 1' and 250 µg of 2, 206.4 µg of 1' and 25 µg of 2, 206.4 µg of 1' and 50 µg of 2, 206.4 µg of 1' and 100 µg of 2, 206.4 µg of 1' and 150 µg of 2, 206.4 µg of 1' and 200 µg of 2, 206.4 µg of 1' and 250 µg of 2, 412.8 µg of 1' and 25 µg of 2, 412.8 µg of 1' and 50 µg of 2, 412.8 µg of 1' and 100 µg of 2, 412.8 µg of 1' and 150 µg of 2, 412.8 µg of 1' and 200 µg of 2, and 412.8 µg of 1' and 250 µg of 2.

If the active substance combination wherein the bromide is used as the salt 1 and 2 denotes one of the preferred steroids disclosed hereinbefore is used as a preferred combination of 1 and 2 according to the invention, the quantities of active substances 1' and 2 administered per single dose as specified by way of example correspond to the following quantities of 1 and 2 administered per single dose: 20 µg of 1 and 25 µg of 2, 20 µg of 1 and 50 µg of 2, 20 µg of 1 and 100 µg of 2, 20 µg of 1 and 150 µg of 2, 20 µg of 1 and 200 µg of 2, 20 µg of 1 and 250 µg of 2, 40 µg of 1 and 25 µg of 2, 40 µg of 1 and 25 µg of 2, 40 µg of 1 and 50 µg of 2, 40 µg of 1 and 100 µg of 2, 40 µg of 1 and 150 µg of 2, 40 µg of 1 and 200 µg of 2, 40 µg of 1 and 250 µg of 2, 60 µg of 1 and 25 µg of 2, 60 µg of 1 and 50 µg of 2, 60 µg of 1 and 100 µg of 2, 60 µg of 1 and 150 µg of 2, 60 µg of 1 and 200 µg of 2, 60 µg of 1 and 250 µg of 2, 100 µg of 1 and 25 µg of 2, 100 µg of 1 and 50 µg of 2, 100 µg of 1 and 100 µg of 2, 100 µg of 1 and 150 µg of 2, 100 µg of 1 and 200 µg of 2, 100 µg of 1 and 250 µg of 2, 200 µg of 1 and 25 µg of 2, 200 µg of 1 and 50 µg of 2, 200 µg of 1 and 100µg of 2, 200 µg of 1 and 150 µg of 2, 200 µg of 1 and 200 µg of 2, 200 µg of 1 and 250 µg of 2, 250 µg of 1 and 25 µg of 2, 250 µg of 1 and 50 µg of 2, 250 µg of 1 and 100 µg of 2, 250 µg of 1 and 150 µg of 2, 250 µg of 1 and 200 µg of 2, 250 µg of 1 and 250 µg of 2, 500 µg of 1 and 25 µg of 2, 500 µg of 1 and 50 µg of 2, 500 µg of 1 and 100 µg of 2, 500 µg of 1 and 150 µg of 2, 500 µg of 1 and 200 µg of 2, and 500 µg of 1 and 250 µg of 2.

At the same time, the ratio of 1 to 3 may be 1:300 to 30:1, preferably from 1:230 to 20:1, more preferably from 1:150 to 10:1, still more preferably from 1:50 to 5:1, and more preferably from 1:35 to 2:1.

In the case of formoterol, for example, the active substance combinations according to the invention may contain 1' and 3' in ratios by weight which are, for example, in the range from about 1:10 to 300:1, preferably 1:5 to 200:1, preferably 1:3 to 150:1, and more preferably from 1:2 to 100:1.

For example and without restricting the scope of the invention thereto, preferred combinations of 1 and 3 according to the invention contain the pharmacologically active cation 1' and formoterol 3' in the following ratios by weight: 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, or 100:1.

The pharmaceutical compositions according to the invention containing the combinations of 1 and 3 are normally used so that the pharmacologically active cation 1' and formoterol 3' are present together in doses from 5 µg to 5000 µg, preferably from 10 µg to 2000 µg, more preferably from 15 µg to 1000 µg, still more preferably from 20 µg to 800 µg, preferably according to the invention from 30 µg to 600 µg, preferably from 40 µg to 500 µg.

For example, the combinations of 1 and 3 according to the invention contain an amount of cation 1' and formoterol 3' such that the total dosage per single dose is about 10 µg, 15 µg, 20 µg, 25 µg, 30 µg, 35 µg, 45 µg, 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, 260 µg, 265 µg, 270 µg, 275 µg, 280 µg, 285 µg, 290 µg, 295 µg, 300 µg, 305 µg, 310 µg, 315 µg, 320 µg, 325 µg, 330 µg, 335 µg, 340 µg, 345 µg, 350 µg, 355 µg, 360 µg, 365 µg, 370 µg, 375 µg, 380 µg, 385 µg, 390 µg, 395 µg, 400 µg, 405 µg, 410 µg, 415 µg, 420 µg, 425 µg, 430 µg, 435 µg, 440 µg, 445 µg, 450 µg, 455 µg, 460 µg, 465 µg, 470 µg, 475 µg, 480 µg, 485 µg, 490 µg, 495 µg, 500 µg, 505 µg, 510 µg, 515 µg, 520 µg, 525 µg, 530 µg, 535 µg, 540 µg, 545 µg, 550 µg, 555 µg, 560 µg, 565 µg, 570 µg, 575 µg, 580 µg, 585 µg, 590 µg, 595 µg, 600 µg, or similar. It is clear to the skilled man that these proposed dosages per single dose are not to be regarded as being restricted to the numerical values explicitly mentioned. Fluctuations of around ±2.5 µg, particularly fluctuations in the decimal range, are also covered as will be apparent to anyone skilled in the art. In these dosage ranges the active substances 1' and 3' are present in the weight ratios described above.

For example and without restricting the scope of the invention thereto, the combinations of 1 and 3 according to the invention contain an amount of cation 1' and formoterol 3' such that they contain, per single dose, for example 8.3 µg of 1' and 2.5 µg of 3', 8.3 µg of 1' and 4.9 µg of 3', 8.3 µg of 1' and 9.8 µg of 3', 8.3 µg of 1' and 14.7 µg of 3', 8.3 µg of 1' and 19.6 µg of 3', 8.3 µg of 1' and 24.4 µg of 3', 16.5 µg of 1 and 2.5 µg of 3', 16.5 µg of 1' and 4.9 µg of 3', 16.5 µg of 1' and 9.8 µg of 3', 16.5 µg of 1' and 14.7 µg of 3', 16.5 µg of 1' and 19.6 µg of 3', 16.5 µg of 1' and 24.4 µg of 3', 33.0 µg of 1' and 2.5 µg of 3', 33.0 µg of 1' and 4.9 µg of 3', 33.0 µg of 1' and 9.8 µg of 3', 33.0 µg of 1' and 14.7 µg of 3', 33.0 µg of 1' and 19.6 µg of 3', 33.0 µg of 1' and 24.4 µg of 3', 49.5 µg of 1' and 2.5 µg of 3', 49.5 µg of 1' and 4.9 µg of 3', 49.5 µg of 1' and 9.8 µg of 3', 49.5 µg of 1' and 14.7 µg of 3', 49.5 µg of 1' and 19.6 µg of 3', 49.5 µg of 1' and 24.4 µg of 3', 82.6 µg of 1' and 2.5 µg of 3', 82.6 µg of 1' and 4.9 µg of 3', 82.6 µg of 1' and 9.8 µg of 3', 8.26 µg of 1' and 14.7 µg of 3', 82.6 µg of 1' and 19.6 µg of 3', 82.6 µg of 1' and 24.4 µg of 3', 165.1 µg of 1' and 2.5 µg of 3', 165.1 µg of 1' and 4.9 µg of 3', 165.1 µg of 1' and 9.8 µg of 3', 165.1 µg of 1' and 14.7 µg of 3', 165.1 µg of 1' and 19.6 µg of 3', 165.1 µg of 1' and 24.4 µg of 3', and 24.4 µg of 3', 206.4 µg of 1' and 2.5 µg of 3', 206.4 µg of 1' and 4.9 µg of 3', 206.4 µg of 1' and 9.8 µg of 3', 206.4 µg of 1' and 14.7 µg of 3', 206.4 µg of 1' and 19.6 µg of 3', 206.4 µg of 1' and 24.4 µg of 3', 412.8 µg of 1' and 2.5 µg of 3', 412.8 µg of 1' and 4.9 µg of 3', 412.8 µg of 1' and 9.8 µg of 3', 412.8 µg of 1' and 14.7 µg of 3', 412.8 µg of 1' and 19.6 µg of 3', and 412.8 µg of 1' and 24.4 µg of 3'.

If the active substance combination wherein the salt 1 is the bromide and 3 denotes formoterol fumarate is used as a preferred combination of 1 and 3 according to the invention, the quantities of active substances 1' and 3 administered per single dose as specified by way of example correspond to the following quantities of 1 and 3 administered per single dose: 10 µg of 1 and 2.9 µg of 3, 10 µg of 1 and 5.7 µg of 3, 10 µg of 1 and 11.5 µg of 3, 10 µg of 1 and 17.2 µg of 3, 10 µg of 1 and 22.9 µg of 3, 10 µg of 1 and 28.5 µg of 3, 20 µg of 1 and 2.9 µg of 3, 20 µg of 1 and 5.7 µg of 3, 20 µg of 1 and 11.5 µg of 3, 20 µg of 1 and 17.2 µg of 3, 20 µg of 1 and 22.9 µg of 3, 20 µg of 1 and 28.5 µg of 3, 40 µg of 1 and 2.9 µg of 3, 40 µg of 1 and 5.7 µg of 3, 40 µg of 1 and 11.5 µg of 3, 40 µg of 1 and 17.2 µg of 3, 40 µg of 1 and 22.9 µg of 3, 40 µg of 1 and 28.5 µg of 3, 60 µg of 1 and 2.9 µg of 3, 60 µg of 1 and 5.7 µg of 3, 60 µg of 1 and 11.5 µg of 3, 60 µg of 1 and 17.2 µg of 3, 60 µg of 1 and 22.9 µg of 3, 60 µg of 1 and 28.5 µg of 3, 100 µg of 1 and 2.9 µg of 3, 100 µg of 1 and 5.7 µg of 3, 100 µg of 1 and 11.5 µg of 3, 100 µg of 1 and 17.2 µg of 3, 100 µg of 1 and 22.9 µg of 3, 100 µg of 1 and 28.5 µg of 3, 200 µg of 1 and 2.9 µg of 3, 200 µg of 1 and 5.7 µg of 3, 200 µg of 1 and 11.5 µg of 3, 200 µg of 1 and 17.2 µg of 3, 200 µg of 1 and 22.9 µg of 3, 200 µg of 1 and 28.5 µg of 3, 250 µg of 1 and 2.9 µg of 3, 250 µg of 1 and 5.7 µg of 3, 250 µg of 1 and 11.5 µg of 3, 250 µg of 1 and 17.2 µg of 3, 250 µg of 1 and 22.9 µg of 3, 250 µg of 1 and 28.5 µg of 3, 500 µg of 1 and 2.9 µg of 3, 500 µg of 1 and 5.7 µg of 3, 500 µg of 1 and 11.5 µg of 3, 500 µg of 1 and 17.2 µg of 3, 500 µg of 1 and 22.9 µg of 3, and 500 µg of 1 and 28.5 µg of 3.

If the active substance combination wherein 3 denotes formoterol fumarate dihydrate and the salt 1 is the bromide is used as a preferred combination of 1 and 3 according to the invention, the quantities of active substances 1' and 3' administered per single dose as specified by way of example correspond to the following quantities of 1 and 3 administered per single dose: 10 µg of 1 and 3 µg of 3, 10 µg of 1 and 6 µg of 3, 10 µg of 1 and 12 µg of 3, 10 µg of 1 and 18 µg of 3, 10 µg of 1 and 24 µg of 3, 10 µg of 1 and 30 µg of 3, 20 µg of 1 and 3 µg of 3, 20 µg of 1 and 6 µg of 3, 20 µg of 1 and 12 µg of 3, 20 µg of 1 and 18 µg of 3, 20 µg of 1 and 24 µg of 3, 20 µg of 1 and 30 µg of 3, 40 µg of 1 and 3 µg of 3, 40 µg of 1 and 6 µg of 3, 40 µg of 1 and 12 µg of 3, 40 µg of 1 and 18 µg of 3, 40 µg of 1 and 24 µg of 3, 40 µg of 1 and 30 µg of 3, 60 µg of 1 and 3 µg of 3, 60 µg of 1 and 6 µg of 3, 60 µg of 1 and 12 µg of 3, 60 µg of 1 and 18 µg of 3, 60 µg of 1 and 24 µg of 3, 60 µg of 1 and 30 µg of 3, 100 µg of 1 and 3 µg of 3, 100 µg of 1 and 6 µg of 3, 100 µg of 1 and 12 µg of 3, 100 µg of 1 and 18 µg of 3, 100 µg of 1 and 24 µg of 3, 100 µg of 1 and 30 µg of 3, 200 µg of 1 and 3 µg of 3, 200 µg of 1 and 6 µg of 3, 200 µg of 1 and 12 µg of 3, 200 µg of 1 and 18 µg of 3, 200 µg of 1 and 24 µg of 3, 200 µg of 1 and 30 µg of 3, 250 µg of 1 and 3 µg of 3, 250 µg of 1 and 6 g of 3, 250 µg of 1 and 12 µg of 3, 250 µg of 1 and 18 µg of 3, 250 µg of 1 and 24 µg of 3, 250 µg of 1 and 30 µg of 3, 500 µg of 1 and 3 µg of 3, 500 µg of 1 and 6 µg of 3, 500 µg of 1 and 12 µg of 3, 500 µg of 1 and 18 µg of 3, 500 µg of 1 and 24 µg of 3, and 500 µg of 1 and 30 µg of 3.

In the case of salmeterol, for example, the active substance combinations according to the invention may contain 1' and 3' in ratios by weight which are in the range from about 1:30 to 400:1, preferably 1:25 to 200:1, preferably 1:20 to 100:1, more preferably from 1:15 to 50: 1, for example.

For example, and without restricting the scope of the invention thereto, the preferred combinations of 1 and 3 according to the invention may contain the cation 1' and salmeterol 3' in the following ratios by weight: 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, or 35:1.

The pharmaceutical compositions according to the invention containing the combinations of 1 and 3 are normally used so that the cation 1' and salmeterol 3' are present together in doses from 5 µg to 5000 µg, preferably from 10 µg to 2000 µg, more preferably from 15 µg to 1000 µg, still more preferably from 20 µg to 800 µg, preferably according to the invention from 30 µg to 750 µg, preferably from 40 µg to 700 µg.

For example, the combinations of 1 and 3 according to the invention contain an amount of 1' and salmeterol 3' such that the total dosage per single dose is about 15 µg, 20 µg, 25 µg, 30 µg, 35 µg, 45 µg, 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, 260 µg, 265 µg, 270 µg, 275 µg, 280 µg, 285 µg, 290 µg, 295 µg, 300 µg, 305 µg, 310 µg, 315 µg, 320 µg, 325 µg, 330 µg, 335 µg, 340 µg, 345 µg, 350 µg, 355 µg, 360 µg, 365 µg, 370 µg, 375 µg, 380 µg, 385 µg, 390 µg, 395 µg, 400 µg, 405 µg, 410 µg, 415 µg, 420 µg, 425 µg, 430 µg, 435 µg, 440 µg, 445 µg, 450 µg, 455 µg, 460 µg, 465 µg, 470 µg, 475 µg, 480 µg, 485 µg, 490 µg, 495 µg, 500 µg, 505 µg, 510 µg, 515 µg, 520 µg, 525 µg, 530 µg, 535 µg, 540 µg, 545 µg, 550 µg, 555 µg, 560 µg, 565 µg, 570 µg, 575 µg, 580 µg, 585 µg, 590 µg, 595 µg, 600 µg, 605 µg, 610 µg, 615 µg, 620 µg, 625 µg, 630 µg, 635 µg, 640 µg, 645 µg, 650 µg, 655 µg, 660 µg, 665 µg, 670 µg, 675 µg, 680 µg, 685 µg, 690 µg, 695 µg, 700 µg or the like. It is clear to the skilled man that these proposed dosages per single dose are not to be regarded as being restricted to the numerical values explicitly mentioned. Fluctuations of around ±2.5 µg, particularly fluctuations in the decimal range, are also covered as will be apparent to anyone skilled in the art. In these dosage ranges the active substances 1' and 3' are present in the weight ratios described above.

For example and without restricting the scope of the invention thereto, the combinations of 1 and 3 according to the invention contain an amount of cation 1' and salmeterol 3' such that they contain, per single dose, for example 8.3 µg of 1' and 12.5 µg of 3', 8.3 µg of 1' and 25 µg of 3', 8.3 µg of 1' and 50 µg of 3', 8.3 µg of 1' and 75 µg of 3', 8.3 µg of 1' and 100 µg of 3', 8.3 µg of 1' and 200 µg of 3', 16.5 µg of 1' and 12.5 µg of 3', 16.5 µg of 1' and 25 µg of 3', 16.5 µg of 1' and 50 µg of 3', 16.5 µg of 1' and 75 µg of 3', 16.5 µg of 1' and 100 µg of 3', 16.5 µg of 1' and 200 µg of 3', 33.0 µg of 1' and 12.5 µg of 3', 33.0 µg of 1' and 25 µg of 3', 33.0 µg of 1' and 50 µg of 3', 33.0 µg of 1' and 75 µg of 3', 33.0 µg of 1' and 100 µg of 3', 33.0 µg of 1' and 200 µg of 3', 49.5 µg of 1' and 12.5 µg of 3', 49.5 µg of 1' and 25 µg of 3', 49.5 µg of 1' and 50 µg of 3', 49.5 µg of 1' and 75 µg of 3', 49.5 µg of 1' and 100 µg of 3', 49.5 µg of 1'0 and 200 µg of 3', 82.6 µg of 1' and 12.5 µg of 3', 82.6 µg of 1' and 25 µg of 3', 82.6 µg of 1' and 50 µg of 3', 82.6 µg of 1' and 75 µg of 3', 82.6 µg of 1' and 100 µg of 3', 82.6 µg of 1' and 200 µg of 3', 165.1 µg of 1' and 12.5 µg of 3', 165.1 µg of 1' and 25 µg of 3', 165.1 µg of 1' and 50 µg of 3', 165.1 µg of 1' and 75 µg of 3', 165.1 µg of 1' and 100 µg of 3', 165.1 µg of 1' and 200 µg of 3', 206.4 µg of 1' and 12.5 µg of 3', 206.4 µg of 1' and 25 µg of 3', 206.4 µg of 1' and 50 µg of 3', 206.4 µg of 1' and 75 µg of 3', 206.4 µg of 1' and 100 µg of 3', 206.4 µg of 1' and 200 µg of 3', 412.8 µg of 1' and 12.5 µg of 3', 412.8 µg of 1' and 25 µg of 3', 412.8 µg of 1' and 50 µg of 3', 412.8 µg of 1' and 75 µg of 3', 412.8 µg of 1' and 100 µg of 3', and 412.8 µg of 1' and 200 µg of 3'.

If the active substance combination wherein the bromide is used as the salt 1 and 3 denotes salmeterol xinafoate is used as a preferred combination of 1 and 3 according to the invention, the quantities of active substances 1' and 3' administered per single dose as specified by way of example correspond to the following quantities of 1 and 3 administered per single dose: 10 µg of 1 and 18.2 µg of 3, 10 µg of 1 and 36.3 µg of 3, 10 µg of 1 and 72.6 µg of 3, 10 µg of 1 and 108.9 µg of 3, 10 µg of 1 and 145.2 µg of 3, 10 µg of 1 and 290.4 µg of 3, 20 µg of 1 and 18.2 µg of 3, 20 µg of 1 and 36.3 µg of 3, 20 µg of 1 and 72.6 µg of 3, 20 µg of 1 and 108.9 µg of 3, 20 µg of 1 and 145.2 µg of 3, 20 µg of 1 and 290.4 µg of 3, 40 µg of 1 and 18.2 µg of 3, 40 µg of 1 and 36.3 µg of 3, 40 µg of 1 and 72.6 µg of 3, 40 µg of 1 and 108.9 µg of 3, 40 µg of 1 and 145.2 µg of 3, 40 µg of 1 and 290.4 µg of 3, 60 µg of 1 and 18.2 µg of 3, 60 µg of 1 and 36.3 µg of 3, 60 µg of 1 and 72.6 µg of 3, 60 µg of 1 and 108.9 µg of 3, 60 µg of 1 and 145.2 µg of 3, 60 µg of 1 and 290.4 µg of 3, 100 µg of 1 and 18.2 µg of 3, 100 µg of 1 and 36.3 µg of 3, 100 µg of 1 and 72.6 µg of 3, 100 µg of 1 and 108.9 µg of 3, 100 µg of 1 and 145.2 µg of 3, 100 µg of 1 and 290.4 µg of 3, 200 µg of 1 and 18.2 µg of 3, 200 µg of 1 and 36.3 µg of 3, 200 µg of 1 and 72.6 µg of 3, 200 µg of 1 and 108.9 µg of 3, 200 µg of 1 and 145.2 µg of 3, 200 µg of 1 and 290.4 µg of 3, 250 µg of 1 and 18.2 µg of 3, 250 µg of 1 and 36.3 µg of 3, 250 µg of 1 and 72.6 µg of 3, 250 µg of 1 and 108.9 µg of 3, 250 µg of 1 and 145.2 µg of 3, 250 µg of 1 and 290.4 µg of 3, 500 µg of 1 and 18.2 µg of 3, 500 µg of 1 and 36.3 µg of 3, 500 µg of 1 and 72.6 µg of 3, 500 µg of 1 and 108.9 µg of 3, 500 µg of 1 and 145.2 µg of 3, and 500 µg of 1 and 290.4 µg of 3.

The quantities of active substance in the pharmaceutical combinations according to the invention can be calculated analogously if instead of salmeterol xinafoate the compounds 3 salmeterol-4-phenylcinnamic acid salt (4-phenylcinnamate) and salmeterol-5-(2,4-difluorophenyl)salicylic acid salt (5-(2,4-difluorophenyl)salicylate; diflunisal) are used, which are equally preferred according to the invention.

The active substance combinations of 1, 2, and 3 according to the invention are preferably administered by inhalation. For this purpose, ingredients 1, 2, and 3 have to be made available in forms suitable for inhalation. Inhalable preparations include inhalable powders, propellant-containing metering aerosols or propellant-free inhalable solutions. Inhalable powders according to the invention containing the combination of active substances 1, 2, and 3 may consist of the active substances on their own or of a mixture of the active substances with physiologically acceptable excipients. Within the scope of the present invention the term carrier may optionally be used instead of the term excipient. Within the scope of the present invention, the term propellant-free inhalable solutions also includes concentrates or sterile inhalable solutions ready for use. The preparations according to the invention may contain the combination of active substances 1, 2, and 3 either together in one formulation or in two or three separate formulations. These formulations which may be used within the scope of the present invention are described in more detail in the next part of the specification.

A. Inhalable Powder Containing the Combinations of Active Substances 1, 2, and 3 According to the Invention The inhalable powders according to the invention may contain 1, 2, and 3 either on their own or in admixture with suitable physiologically acceptable excipients.

If the active substances 1, 2, and 3 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, or maltose), oligo- and polysaccharides (e.g., dextran), polyalcohols (e.g., sorbitol, mannitol, or xylitol), salts (e.g., sodium chloride or calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 µm and 150 µm, most preferably between 15 µm and 80 µm. It may sometimes seem appropriate to add finer excipient fractions with an average particle size of 1 µm to 9 µm to the excipients mentioned above. These finer excipients are also selected from the group of possible excipients listed hereinbefore. Finally, in order to prepare the inhalable powders according to the invention, micronised active substance 1, 2, and 3, preferably with an average particle size of 0.5 µm to 10 µm, more preferably from 1 µm to 5 µm, is added to the excipient mixture. Processes for producing the inhalable powders according to the invention by grinding and micronizing and lastly mixing the ingredients together are known from the prior art. The inhalable powders according to the invention may be prepared and administered either in the form of a single powder mixture which contains 1, 2, and 3 or in the form of separate inhalable powders which contain only 1, 2, or 3.

The inhalable powders according to the invention may be administered using inhalers known from the prior art. Inhalable powders according to the invention which contain a physiologically acceptable excipient in addition to 1, 2, and 3 may be administered, for example, by means of inhalers which deliver a single dose from a supply using a measuring chamber as described in U.S. Pat. No. 4,570,630, or by other means as described in DE 36 25 685 A. Preferably, the inhalable powders according to the invention which contain physiologically acceptable excipients in addition to 1, 2, and 3 are packed into capsules (to produce so-called inhalettes) which are used in inhalers as described, for example, in WO 94/28958, which is equivalent to U.S. Pat. No. 5,947,118, both of which are hereby incorporated by reference in their entireties.

A particularly preferred inhaler for using the pharmaceutical combination according to the invention in inhalettes is shown in FIG. 1.

This HANDIHALER® inhaler for inhaling powdered pharmaceutical compositions from capsules is characterized by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut and air holes 13 for adjusting the flow resistance.

If the inhalable powders according to the invention are to be packed into capsules (inhalettes) for the preferred use described above, the quantities packed into each capsule should be 1 mg to 30 mg, preferably 3 mg to 20 mg, more particularly 5 mg to 10 mg of inhalable powder per capsule. These capsules contain, according to the invention, either together or separately, the doses of 1, 2, and 3 mentioned hereinbefore for each single dose.

B. Propellant Gas-Driven Inhalation Aerosols Containing the Combinations of Active Substances 1, 2, and 3 According to the Invention Inhalation aerosols containing propellant gas according to the invention may contain substances 1, 2, and 3 dissolved in the propellant gas or in dispersed form. 1, 2, and 3 may be present in separate formulations or in a single preparation, in which 1, 2, and 3 are either each dissolved, dispersed or only one or two of the components is or are dissolved and the other or others is or are dispersed. The propellant gases which may be used to prepare the inhalation aerosols according to the invention are known from the prior art. Suitable propellant gases are selected from among hydrocarbons such as n-propane, n-butane, or isobutane and halohydrocarbons such as fluorinated derivatives of methane, ethane, propane, butane, cyclopropane, or cyclobutane. The propellant gases mentioned above may be used on their own or in mixtures thereof. Particularly preferred propellant gases are halogenated alkane derivatives selected from TG134a, TG227, and mixtures thereof.

The propellant-driven inhalation aerosols according to the invention may also contain other ingredients such as co-solvents, stabilizers, surfactants, antioxidants, lubricants, preservatives, and pH adjusters. All these ingredients are known in the art.

The inhalation aerosols containing propellant gas according to the invention may contain up to 5 wt.-% of active substance 1, 2, and/or 3. Aerosols according to the invention contain, for example, 0.002 to 5 wt.-%, 0.01 to 3 wt.-%, 0.015 to 2 wt.-%, 0.1 to 2 wt.-%, 0.5 to 2 wt.-%, or 0.5 to 1 wt.-% of active substance 1, 2, and/or 3.

If the active substances 1, 2, and/or 3 are present in dispersed form, the particles of active substance preferably have an average particle size of up to 10 µm, preferably from 0.1 µm to 5 µm, more preferably from 1 µm to 5 µm.

The propellant-driven inhalation aerosols according to the invention mentioned above may be administered using metered dose inhalers (MDI) known in the art. Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterized in that they contain the propellant gas-containing aerosols described above according to the invention. The present invention also relates to cartridges which are fitted with a suitable valve and can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C. Propellant-Free Inhalable Solutions or Suspensions Containing the Combinations of Active Substances 1, 2, and 3 According to the Invention It is particularly preferred to use the active substance combination according to the invention in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1, 2 and 3, separately or together, are adjusted to a pH of 2 to 7, preferably 2 to 5, using suitable acids. The pH may be adjusted using acids selected from inorganic or organic acids. Examples of suitable inorganic acids include hydrochloric acid, hydrobromic acid, nitric acid, sulfuric acid and/or phosphoric acid. Examples of particularly suitable organic acids include ascorbic acid, citric acid, malic acid, tartaric acid, maleic acid, succinic acid, fumaric acid, acetic acid, formic acid, and/or propionic acid, etc. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may be used, particularly in the case of acids which have other properties in addition to their acidifying qualities, e.g., as flavorings, antioxidants, or complexing agents, such as citric acid or ascorbic acid, for example. According to the invention, it is particularly preferred to use hydrochloric acid to adjust the pH.

According to the invention, the addition of edetic acid (EDTA) or one of the known salts thereof, sodium edetate, as stabilizer or complexing agent is unnecessary in the present formulation. Other embodiments may contain this compound or these compounds. In a preferred embodiment the content based on sodium edetate is less than 100 mg/100 mL, preferably less than 50 mg/100 mL, more preferably less than 20 mg/100 mL. Generally, inhalable solutions in which the content of sodium edetate is from 0 to 10 mg/100 mL are preferred.

Co-solvents and/or other excipients may be added to the propellant-free inhalable solutions according to the invention. Preferred co-solvents are those which contain hydroxyl groups or other polar groups, e.g., alcohols, particularly isopropyl alcohol, glycols, particularly propyleneglycol, polyethyleneglycol, polypropyleneglycol, glycol ether, glycerol, polyoxyethylene alcohols, and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants, and/or preservatives which guarantee or prolong the shelf life of the finished pharmaceutical formulation, flavorings, vitamins and/or other additives known in the art. The additives also include physiologically acceptable salts such as sodium chloride as isotonic agents. The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 mL, more preferably between 5 and 20 mg/100 mL.

Preferred formulations contain, in addition to the solvent water and the combination of active substances 1, 2, and 3, only benzalkonium chloride and sodium edetate. In another preferred embodiment, no sodium edetate is present.

The propellant-free inhalable solutions according to the invention are administered in particular using inhalers of the kind which are capable of nebulizing a small amount of a liquid formulation in the required therapeutic dose within a few seconds to produce an aerosol suitable for therapeutic inhalation. Within the scope of the present invention, preferred nebulizers are those in which a quantity of less than 100 µL, preferably less than 50 µL, more preferably between 20 µL and 30 µL of active substance solution can be nebulized in preferably one spray action to form an aerosol with an average particle size of less than 20 µm, preferably less than 10 µm, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf, in particular, FIGS. 6a and 6b). The nebulizers (devices) described therein are known by the name RESPIMAT®. WO 91/14468 is equivalent to U.S. Pat. Nos. 5,457,944 and 5,662,271; and WO 97/12687 is equivalent to U.S. Pat. Nos. 5,964,416, 6,402,055, and 6,497,373, all of which are hereby incorporated by reference in their entireties.

This RESPIMAT® nebulizer can advantageously be used to produce the inhalable aerosols according to the invention containing the combination of active substances 1, 2, and 3. Because of its cylindrical shape and handy size of less than 9 cm to 15 cm long and 2 cm to 4 cm wide, this device can be carried at all times by the patient. The nebulizer sprays a defined volume of pharmaceutical formulation using high pressures through small nozzles so as to produce inhalable aerosols.

The preferred atomizer essentially consists of an upper housing part, a pump housing, a nozzle, a locking mechanism, a spring housing, a spring, and a storage container, characterized by:
- a pump housing which is secured in the upper housing part and which comprises at one end a nozzle body with the nozzle or nozzle arrangement,
- a hollow plunger with valve body,
- a power takeoff flange in which the hollow plunger is secured and which is located in the upper housing part,
- a locking mechanism situated in the upper housing part,
- a spring housing with the spring contained therein, which is rotatably mounted on the upper housing part by means of a rotary bearing, and
- a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 MPa to 60 MPa (about 50 bar to 600 bar), preferably 10 MPa to 60 MPa (about 100 bar to 600 bar) on the fluid, the measured amount of active substance solution, at its high pressure end at the moment when the spring is actuated. Volumes of 10 to 50 microliters are preferred, while volumes of 10 to 20 microliters are particularly preferred and a volume of 15 microliters per spray is most particularly preferred.

The valve body is preferably mounted at the end of the hollow plunger facing the nozzle body.

The nozzle in the nozzle body is preferably microstructured, i.e., produced by microtechnology. Microstructured nozzle bodies are disclosed, for example, in WO 94/07607, particularly FIG. 1 therein and the associated description. WO 94/07607 is equivalent to U.S. Pat. Nos. 5,911,851; 6,007,676; and 6,503,362, all of which are hereby incorporated by reference in their entireties.

The nozzle body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20° to 160° to one another, preferably 600 to 1500, most preferably 80° to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 bar to 300 bar, and is atomized into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g., a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomizer axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomizer; this causes the deformable ring to deform in the annular plane. Details of the construction of the locking mechanism are given in WO 97/20590.

The lower housing part is pushed axially over the spring housing and covers the mounting, the drive of the spindle and the storage container for the fluid.

When the atomizer is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360°, e.g., 180°. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomized may be pushed into the atomizer one after another and used in succession. The storage container contains the aqueous aerosol preparation according to the invention.

The atomizing process is initiated by pressing gently on the actuating button. As a result, the locking mechanism opens up the path for the power takeoff member. The biased spring pushes the plunger into the cylinder of the pump housing. The fluid leaves the nozzle of the atomizer in atomized form.

Further details of construction are disclosed in PCT Applications WO 97/12683 and WO 97/20590, to which reference is hereby made. WO 97/12683 is equivalent to U.S. Pat. No. 6,176,442; and WO 97/20590 is equivalent to U.S. Pat. No. 6,453,795, all of which are hereby incorporated by reference in their entireties.

The components of the atomizer (nebulizer) are made of a material which is suitable for its purpose. The housing of the atomizer and, if its operation permits, other parts as well, are preferably made of plastics, e.g., by injection molding. For medicinal purposes, physiologically safe materials are used.

Figure 2A:
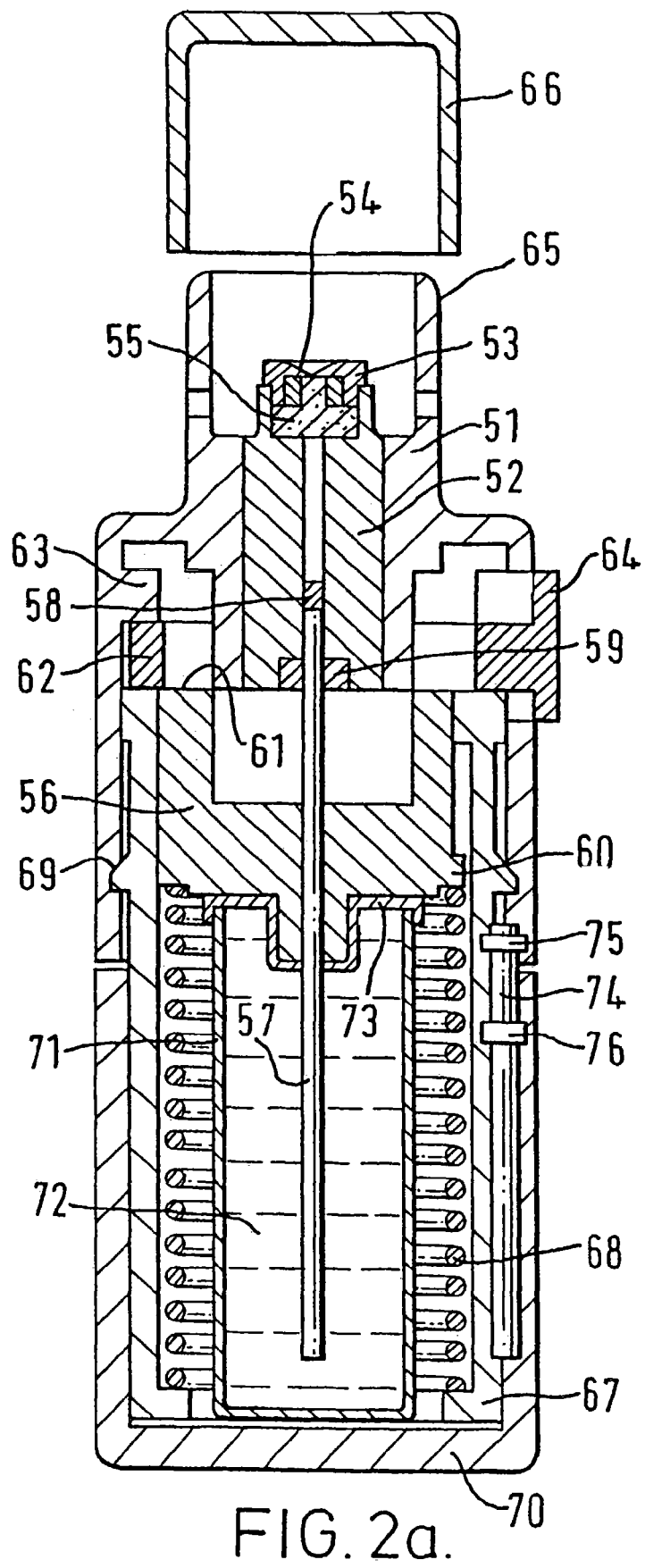

FIGS. 2a/b attached hereto, which are identical to FIGS. 6a/b of WO 97/12687, show the RESPIMAT® nebulizer which can advantageously be used for inhaling the aqueous aerosol preparations according to the invention.

Figure 2B:
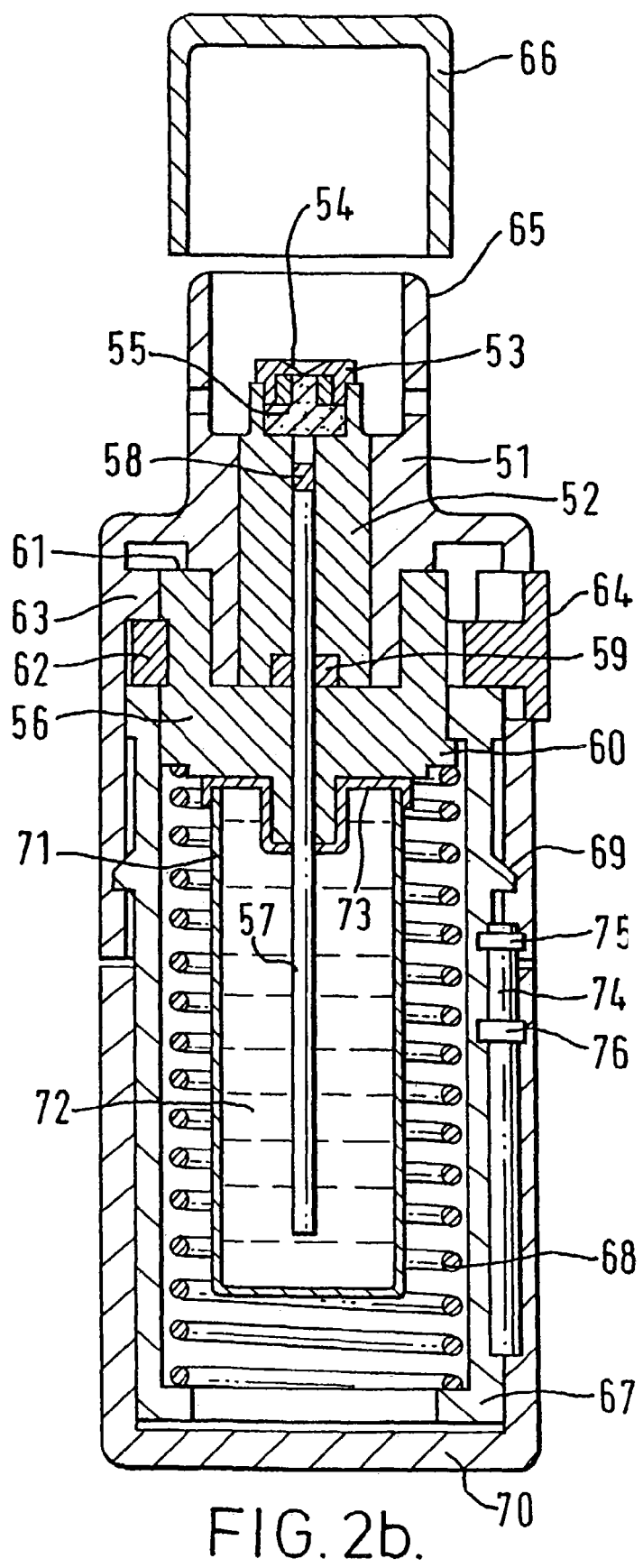

FIG. 2a shows a longitudinal section through the atomizer with the spring biased while FIG. 2b shows a longitudinal section through the atomizer with the spring relaxed.

The upper housing part (51) contains the pump housing (52) on the end of which is mounted the holder (53) for the atomizer nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomized. The storage container is sealed off by the stopper (73) through which the hollow plunger projects into the storage container and is immersed at its end in the fluid (supply of active substance solution). The spindle (74) for the mechanical counter is mounted in the covering of the spring housing. At the end of the spindle facing the upper housing part is the drive pinion (75). The slider (76) sits on the spindle.

The nebulizer described above is suitable for nebulizing the aerosol preparations according to the invention to produce an aerosol suitable for inhalation.

If the formulation according to the invention is nebulized using the method described above (with the RESPIMAT® nebulizer) the quantity delivered should correspond to a defined quantity with a tolerance of not more than 25%, preferably 20% of this amount in at least 97%, preferably at least 98% of all operations of the inhaler (spray actuations). Preferably, between 5 mg and 30 mg of formulation, most preferably between 5 mg and 20 mg of formulation are delivered as a defined mass on each actuation.

However, the formulation according to the invention may also be nebulized by means of inhalers other than those described above, e.g., jet stream inhalers.

Accordingly, in a further aspect, the invention relates to pharmaceutical formulations in the form of propellant-free inhalable solutions or suspensions as described above combined with a device suitable for administering these formulations, preferably in conjunction with the RESPIMAT® nebulizer. Preferably, the invention relates to propellant-free inhalable solutions or suspensions characterized by the combination of active substances 1, 2, and 3 according to the invention in conjunction with the RESPIMAT(®) nebulizer. In addition, the present invention relates to the above-mentioned devices for inhalation, preferably the RESPIMAT® nebulizer, characterized in that they contain the propellant-free inhalable solutions or suspensions according to the invention as described hereinbefore.

The propellant-free inhalable solutions or suspensions according to the invention may take the form of concentrates or sterile inhalable solutions or suspensions ready for use, as well as the above-mentioned solutions and suspensions designed for use in a RESPIMAT® nebulizer. Formulations ready for use may be produced from the concentrates, for example, by the addition of isotonic saline solutions. Sterile formulations ready for use may be administered using energy-operated fixed or portable nebulizers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterized in that the device is an energy-operated free-standing or portable nebulizer which produces inhalable aerosols by means of ultrasound or compressed air by the Venturi principle or other methods.

The Examples which follow serve to illustrate the present invention in more detail without restricting the scope of the invention to the following embodiments by way of example.

EXAMPLES OF FORMULATIONS

| Ingredients | μg per capsule |
|---|---|
| 1. Inhalable Powder | |
| 1'-bromide | 100 |
| budesonide | 200 |
| salmeterol xinafoate | 55.9 |
| lactose | 4644.1 |
| Total | 5000 |
| 2. Inhalable Powder | |
| 1'-bromide | 75 |
| fluticasone propionate | 125 |
| salmeterol-4-phenylcinnamate | 50 |
| lactose | 4650 |
| Total | 5000 |
| 3. Inhalable Powder | |
| 1'-bromide | 75 |
| mometasone furoate | 250 |
| formoterol fumarate dihydrate | 12 |
| lactose | 4663 |
| Total | 5000 |
| 4. Inhalable Powder | |
| 1'-bromide | 100 |
| fluticasone propionate | 250 |
| formoterol fumarate dihydrate | 12 |
| lactose | 4638 |
| Total | 5000 |
| 5. Inhalable Powder | |
| 1'-bromide | 200 |
| formoterol fumarate dihydrate | 12 |
| fluticasone propionate | 250 |
| lactose | 24538 |
| Total | 25000 |
| 6. Inhalable Powder | |
| 1'-bromide | 75 |
| fluticasone propionate | 125 |
| salmeterol-diflunisal | 50 |
| lactose | 24750 |
| Total | 25000 |

-continued

| Ingredients | wt.-% |
|---|---|
| 7. Suspension Aerosol Containing Propellant Gas | |
| 1'-bromide | 0.035 |
| budesonide | 0.4 |
| formoterol fumarate dihydrate | 0.066 |
| soya lecithin | 0.2 |
| TG 134a:TG227 (2:3) | to 100 |
| 8. Suspension Aerosol Containing Propellant Gas | |
| 1'-bromide | 0.039 |
| fluticasone propionate | 0.3 |
| salmeterol xinafoate | 0.033 |
| isopropyl myristate | 0.1 |
| TG 227 | to 100 |
| 9. Suspension Aerosol Containing Propellant Gas | |
| 1'-bromide | 0.039 |
| mometasone furoate | 0.6 |
| salmeterol-diflunisal | 0.066 |
| isopropyl myristate | 0.1 |
| TG 227 | to 100 |
| 10. Suspension Aerosol Containing Propellant Gas | |
| 1'-bromide | 0.035 |
| fluticasone propionate | 0.3 |
| salmeterol 4-phenylcinnamate | 0.066 |
| soya lecithin | 0.2 |
| TG 11:TG12 (2:3) | to 100 |
| 11. Suspension Aerosol Containing Propellant Gas | |
| 1'-bromide | 0.039 |
| salmeterol xinafoate | 0.033 |
| budesonide | 0.4 |
| absolute ethanol | 0.5 |
| isopropyl myristate | 0.1 |
| TG 227 | to 100 |

We claim:

1. A pharmaceutical composition comprising:
   (a) an anticholinergic of formula 1

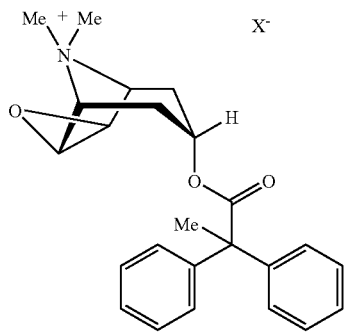

wherein $X^-$ is an anion with a single negative charge,
   (b) a corticosteroid; and
   (c) a betamimetic,
wherein each component (a), (b), and (c) is optionally in the form of a solvate or hydrate thereof.

2. The pharmaceutical composition according to claim 1, further comprising a physiologically acceptable excipient.

3. The pharmaceutical composition according to claim 2, wherein the physiologically acceptable excipient is a monosaccharide, disaccharide, oligo- or polysaccharide, polyalcohol, salt, or mixture thereof.

4. The pharmaceutical composition according to claim 1, wherein: $X^-$ is selected from the group consisting of: chloride, bromide, iodide, sulfate, phosphate, methanesulfonate, nitrate, maleate, acetate, citrate, fumarate, tartrate, oxalate, succinate, benzoate, and p-toluenesulfonate.

5. The pharmaceutical composition according to claim 1, wherein: $X^-$ is selected from the group consisting of: chloride, bromide, methanesulfonate, and p-toluenesulfonate.

6. The pharmaceutical composition according to claim 1, wherein $X^-$ is bromide.

7. The pharmaceutical composition according to claim 1, wherein the corticosteroid is selected from flunisolide, beclomethasone, triamcinolone, budesonide, fluticasone, mometasone, ciclesonide, rofleponide, GW215864, KSR592, ST-126, dexamethasone, and mixtures thereof.

8. The pharmaceutical composition according to claim 1, wherein the corticosteroid is selected from flunisolide, beclomethasone, triamcinolone, budesonide, fluticasone, mometasone, ciclesonide, dexamethasone, and mixtures thereof.

9. The pharmaceutical composition according to claim 1, wherein the betamimetic is selected from bambuterol, bitolterol, carbuterol, clenbuterol, fenoterol, formoteri, hexoprenaline, ibuterol, pirbuterol, procaterol, reproterol, salmeterol, sulfonterol, terbutaline, tolubuterol, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino5ethanol, 1-[2H-5-hydroxy-3-oxo-4H-1,4-benzoxazin-8-yl]-2-[3-(4-n-butyloxyphenyl)-2-methyl-2-propylamino ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H- 1,4-benzoxazin-3-(4H)-one, 1-(4-amino-3-chloro-5-trifluoromethylphenyl)-2-tert-butylamino)ethanol, 1-(4-ethoxycarbonylamino-3-cyano-5-fluorophenyl)-2-(tert-butylamino)ethanol, and mixtures thereof.

10. The pharmaceutical composition according to claim 1, wherein the betamimetic is selected from formoterol, salmeterol, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2F1-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, and mixtures thereof.

11. The pharmaceutical composition according to one of claims 1 to 10, wherein the weight ratio of the anticholinergic in the form of its cation to the corticosteroid is in the range from 1:250 to 250:1.

12. The pharmaceutical composition according to one of claims 1 to 10, wherein the weight ratio of anticholinergic to the betamimetic is in the range from 1:300 to 30:1.

13. The pharmaceutical composition according to one of claims 1 to 10, wherein the total amount of the anticholinergic, the corticosteroid, and the betamimetic is 1 μg to 10000 μg.

14. The pharmaceutical composition according to claim 1, wherein the total amount of the anticholinergic, the corticosteroid, and the betamimetic is 10 μg to 2000 μg.

15. The pharmaceutical composition according to claim 1, wherein the pharmaceutical composition is in a form suitable for inhalation.

16. The pharmaceutical composition according to claim 15, wherein the pharmaceutical composition is an inhalable powder, or a propellant-free inhalable solution or suspension.

17. The pharmaceutical composition according to one of claims 2 to 10, wherein the pharmaceutical composition is in a form suitable for inhalation.

18. The pharmaceutical composition according to one of claims 2 or 3, wherein the pharmaceutical composition is an inhalable powder and the physiologically acceptable excipient has a maximum average particle size of up to 250 μm.

19. The pharmaceutical composition according to claim 18, wherein the physiologically acceptable excipient has a maximum average particle size of between 10 μm and 150 μm.

20. A capsule containing inhalable powder according to claim 18.

21. A pharmaceutical composition consisting essentially of:
(a) an anticholinergic of formula 1

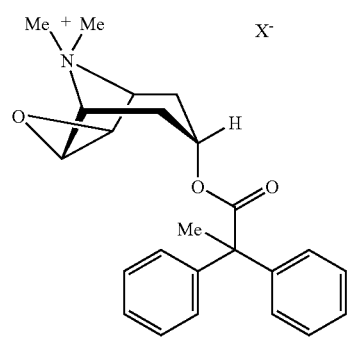

wherein $X^-$ is an anion with a single negative charge;
(b) a corticosteroid; and
(c) a betamimetic,
wherein each component (a), (b), and (c) are optionally in the form of the solvates or hydrates thereof.

* * * * *